US010363376B2

(12) United States Patent
Mantsch et al.

(10) Patent No.: US 10,363,376 B2
(45) Date of Patent: Jul. 30, 2019

(54) SAFETY DEVICE FOR A MEDICAL NEEDLE

(71) Applicant: OMT GmbH & Co., KG, Frittlingen (DE)

(72) Inventors: Christian Mantsch, Minden (DE); Uwe Stumpp, Frittlingen (DE)

(73) Assignee: OMT GmbH & Co. KG, Frittlingen (DE)

( * ) Notice: Subject to any disclaimer, the term of this patent is extended or adjusted under 35 U.S.C. 154(b) by 127 days.

(21) Appl. No.: 14/847,458

(22) Filed: Sep. 8, 2015

(65) Prior Publication Data

US 2016/0074596 A1 Mar. 17, 2016

(30) Foreign Application Priority Data

Sep. 12, 2014 (DE) .................... 20 2014 104 338 U

(51) Int. Cl.
*A61M 5/32* (2006.01)
*A61M 5/158* (2006.01)
*A61M 25/06* (2006.01)

(52) U.S. Cl.
CPC .......... *A61M 5/3202* (2013.01); *A61M 5/158* (2013.01); *A61M 5/32* (2013.01); *A61M 5/3275* (2013.01); *A61M 25/0625* (2013.01); *A61M 25/0637* (2013.01); *A61M 2005/1581* (2013.01); *A61M 2005/325* (2013.01); *A61M 2005/3247* (2013.01)

(58) Field of Classification Search
CPC ...... A61M 5/3202; A61M 5/158; A61M 5/32; A61M 5/3275; A61M 2005/1581; A61M 2005/3247; A61M 2005/325; A61M 25/0625; A61M 25/0637

See application file for complete search history.

(56) References Cited

U.S. PATENT DOCUMENTS 6,997,902 B2 * 2/2006 Thorne ................. A61M 5/158
604/110
7,125,398 B2 * 10/2006 Garcia, Jr. ............ A61M 5/158
604/263

(Continued)

FOREIGN PATENT DOCUMENTS

DE  60014151 T2  10/2005
EP  1682202 B1   7/2006

(Continued)

*Primary Examiner* — Kevin C Sirmons
*Assistant Examiner* — Tezita Z Watts
(74) *Attorney, Agent, or Firm* — Richard M. Goldberg

(57) ABSTRACT

A safety device for shielding a medical needle, includes a hand grip element; a cannula held at the hand grip element; a base with laterally protruding, flat wings, the base having a guide opening which is spaced apart from the underside and in which the cannula is guided; and a connecting structure which connects the handle element with the base and includes two elongated sections connected in a row with one another by at least one joint and the connecting structure is connected at one end by at least one joint with the hand grip element and, at the other end, by at least one joint with the base, the elongated section of the connecting structure, which is connected with the base has a wall element which protrudes transversely at its base end, and the connecting structure can be unfolded from a first state into a second extended state.

14 Claims, 5 Drawing Sheets

(56) References Cited

U.S. PATENT DOCUMENTS

| | | | |
|---|---|---|---|
| 7,291,135 B2* | 11/2007 | Ono | A61M 5/158 |
| | | | 604/263 |
| 7,347,842 B2 | 3/2008 | Thorne et al. | |
| 7,351,230 B2 | 4/2008 | Smith et al. | |
| 7,758,544 B2 | 7/2010 | Solomon et al. | |
| 2005/0049553 A1 | 3/2005 | Triplett et al. | |
| 2006/0064061 A1 | 3/2006 | Solomon et al. | |
| 2009/0131876 A1* | 5/2009 | Coyne | A61M 5/3216 |
| | | | 604/198 |
| 2013/0172826 A1* | 7/2013 | Morita | A61M 5/00 |
| | | | 604/263 |

FOREIGN PATENT DOCUMENTS

| | | |
|---|---|---|
| EP | 2206528 A1 | 7/2010 |
| EP | 2332594 A2 | 6/2011 |
| EP | 2609953 A1 | 7/2013 |
| WO | 2009046560 A2 | 4/2009 |
| WO | 2010101573 A1 | 9/2010 |

* cited by examiner

SAFETY DEVICE FOR A MEDICAL NEEDLE

BACKGROUND OF THE INVENTION

The invention relates to a safety device for shielding a medical needle, with a hand grip element, a cannula held thereon and a base with laterally protruding, flat wings, the underside of the base being essentially flat and the base having a guide opening, in which the cannula is guided, as well as a foldable connecting structure, which connects the hand grip element with the base.

EP 1 682 202 B1 describes a shielding device for a medical needle, with shielding, which can be extended from an inserted position into an extended position in order to surround a distal end of a needle. The device comprises an external bearing and a separate internal bearing, which can be moved in an internal space of the external bearing along the longitudinal axis. A supple retaining rope, constructed of several segments, connects the outer bearing with a hub, at which a cannula, in the form of a Huber needle, is mounted. A wedging section, which can be moved along with the inner bearing, contains a cam face, which engages a sidewall of the outer bearing, in order to rotate the wedging section and wedge it with respect to the needle, when the inner bearing is pulled upward within the outer bearing. The wedging section is swiveled about an axis, which is disposed transversely to the joint axes of hinges of the retaining rope. The retaining rope prevents the shielding being pulled from the needle, when the latter is in the extended position.

EP 2 206 528 A1, EP 2 332 594 A2, U.S. Pat. Nos. 6,997,902 B2, 7,347,842 B2, 7,351,230 B2 and 7,758,544 B2 describe similar shielding devices.

SUMMARY OF THE INVENTION

It is an object of the invention to provide a safety device for a medical port needle, the device being distinguished owing to the fact that, after use, it protects the needle particularly well against access.

Pursuant to the invention, this objective is accomplished by a safety device for shielding a medical needle comprising:
- a hand grip element;
- a cannula, which is held at the hand grip element;
- a base with laterally protruding flat wings, the underside of the base, which extends over the wings, being essentially flat and the base having a guide opening, which is spaced apart from the underside and in which the cannula is guided,
- a connecting structure, which connects the hand grip element with the base and two elongated sections, which are connected with one another in a row by means of at least one joint, the connecting structure being connected at one end by means of at least one joint with the hand grip element and, at the other end, by means of at least one joint, with the base;
- the elongated section of the connecting structure, which is connected with the base by means of at least one joint, having a wall element, which protrudes transversely at its base end, and
- and the sections and the joints being disposed, so that the connecting structure can be unfolded from a first state, in which the cannula, which is guided in the guide opening of the base and protrudes from the underside of the base with the tip of the cannula, can be unfolded into a second extended state, in which the cannula is disposed along the connecting structure, the wall element is disposed transversely in front of the tip of the cannula and a side wall of the base protectively surrounds the tip between the guide opening and the wall element and shields it against access.

By holding the base at the wings and pulling up the hand grip element, the connecting structure is unfolded and, at the same time, the cannula is pulled up together with the hand grip element. While the lower elongated section of the lower elongated section of the connecting structure, which is connected with the base by the at least one joint, is raised as the connecting structure is being folded, the wall element thereof, protruding transversely therefrom, is swiveled together with the section. That is, the wall element, which is coupled directly with the lower section and preferably is permanently connected with the lower section, is swiveled together with the latter, so that, already by unfolding the connecting structure, the wall element assumes its final position, in which it is in front of the tip of the cannula. By these means, it is ensured that, in the extended state of the connecting structure, the wall element is transversely in front of the tip of the cannula. This corresponds to the safe condition of the safety device, in which the tip of the cannula is disposed between the guide opening and the wall element and thus shielded against access. Accordingly, the unfolding of the connecting structure into the extended state automatically brings the safety device into the safe condition. It is particularly advantageous that a very small number of movable parts nevertheless make it possible to shield the tip of the cannula safely. For example, the wall element, which protrudes transversely, may be formed in one piece with the elongated section of the connecting structure. While the wall element, which protrudes transversely, and the elongated section of the connecting structure, at which it is disposed, are swiveled jointly, there is a high functional reliability of the shielding.

Preferred embodiments of the invention arise out of the dependent claims.

Preferably, the sections of the connecting structure in each case comprise two parts, especially two parts in the form of shielding walls, which are mutually opposite one another on either side of the cannula, next to which they are disposed in the longitudinal direction of the cannula when the connecting structure is extended in the second state. The parts, disposed on either side of the cannula, protect the cannula against lateral contact.

Preferably, the parts have shielding walls, the flat sides of which are opposite to one another. By these means, the cannula can be shielded particularly well against contact. After all, the shielding walls, which extend in the longitudinal direction of the respective section, shield, a space, which stretches between them, against contact.

Preferably, a first elongated section of the connecting structure is connected at one end with the hand grip element and, at the other end, with the second of the elongated sections, in each case over at least one joint in the form of a living hinge. By these means, the construction of the connecting structure can be simplified.

Preferably, the elongated section of the connecting structure, which is connected with the base by means of at least one joint, has kingpins, which are mounted in the receivers of the base, the joint pins and the receivers forming the at least one joint. This makes it possible to produce the connecting structure and the base from materials of different hardness. In addition, it is possible to form a particularly stable joint in this way.

Preferably, the hand grip element, the elongated sections of the connecting structure, the wall element and the kingpin are formed together in one piece from plastic.

By these means, a simplified and particular compact construction is made possible. Preferably, the elongated section of the connecting structure, connected with the base by means of at least one joint, is divided in the longitudinal direction, the two parts of the base end of the section being firmly connected over the transversely protruding wall element and the section, on mutually opposite sides, having kingpins, which form the axis of the joint, the two parts, as seen in the direction of the joint axis, forming an L-shaped arrangement with the wall section. Preferably, the joint axis passes through the angle of the L shape. By these means, the swiveling motion of the section, in its position in front of the tip of the cannula, is converted particularly efficiently into a swiveling motion of the wall element when the connecting structure is unfolded.

Preferably, the connecting structure is divided along its longitudinal direction and the division extends over the connection of the two longitudinal sections, so that the connecting structure has two parts in each of the sections, the sections being connected, by a joint in the form of two living hinges, each of which connects one part of the one section with one part of the other section, the parts of a respective section being disposed opposite to one another, extending on either side of the cannula and next to the latter in the longitudinal direction of the cannula, when the connecting structure is extended linearly in the second state. Due to this divided construction of the connecting structure, the latter can be unfolded past the cannula.

Preferably, the base has at least one blocking element, which, when the connecting structure is extended linearly in the second state, is disposed behind the section of the connecting structure, which is connected with the base by means of a joint, so that this section is blocked against being folded back. The blocking element may, for example, be a wedge, over which the section of the connecting structure can be moved with elastic deformation of the wedge and or of the section, when the connecting structure is unfolded from the first into the second state. Alternatively or additionally to the blocking element, the base preferably has a stopping projection, which, when the connecting structure is extended linearly in the second state, is disposed under the wall element of the section, which is connected with the base by means of a joint, so that this section is blocked against being folded back. The connecting structure can be protected simply and effectively by the blocking element and/or the stopping projection against being folded together once again.

BRIEF DESCRIPTION OF THE DRAWINGS

A preferred example of the invention is described in greater detail in the following by means of the drawing, in which.

DETAILED DESCRIPTION

Figure 1:
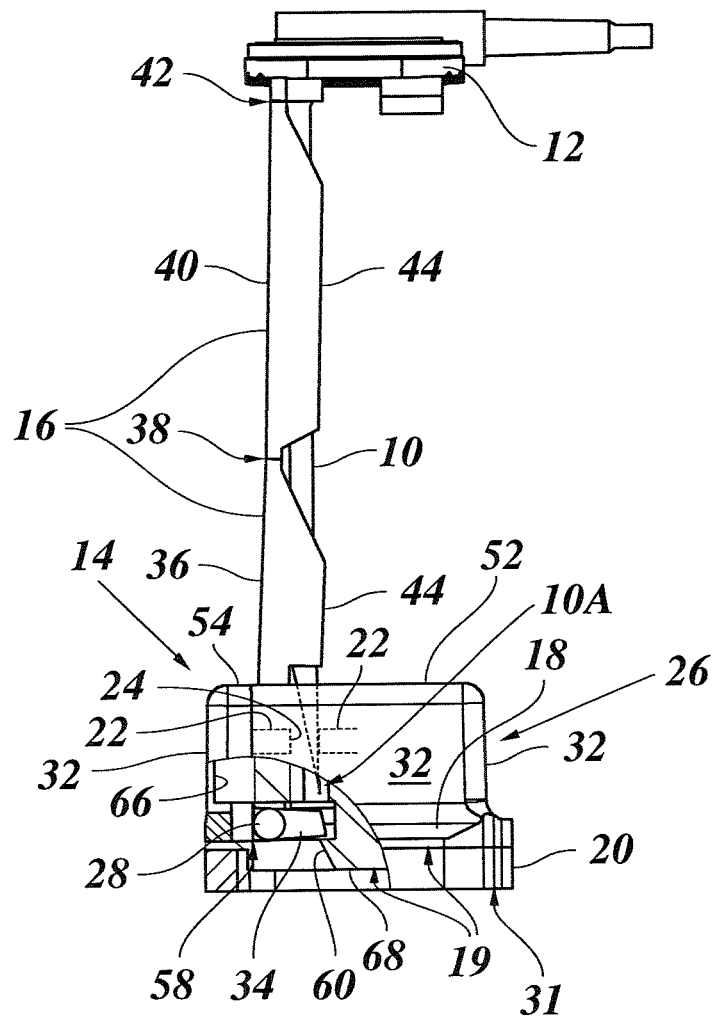
FIG. 1 shows a diagrammatic side view, partly in sectional representation, of an inventive safety device in a safe state.
Figure 4:
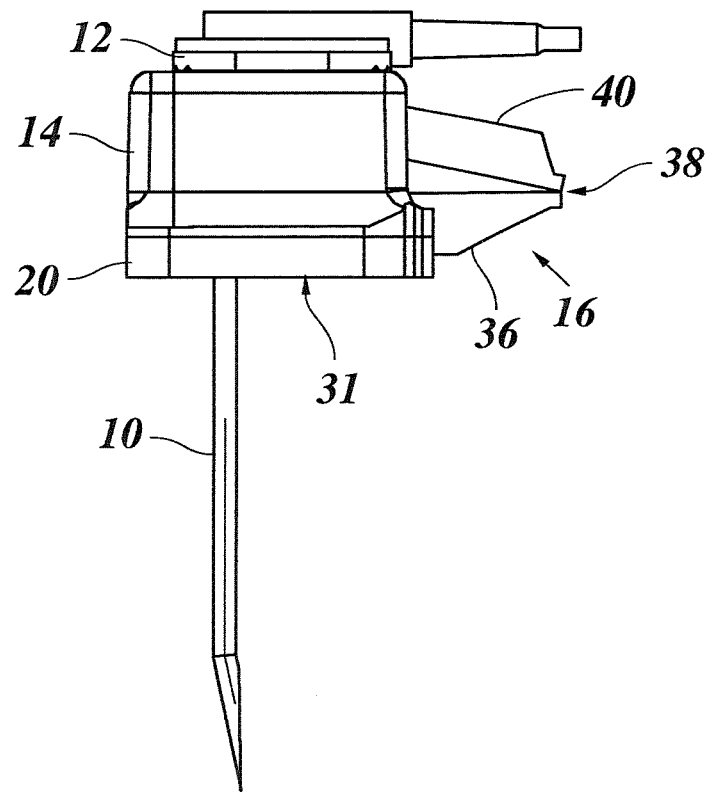
FIG. 4 shows the safety device in a ready to use state of a port needle in a view corresponding to that of FIG. 1.

FIG. 1 shows an inventive safety device for shielding a medical needle, especially a port needle 10, with a hand grip element 12, a base 14 and a connecting structure 16, which connects the handle element 12, with the base 14. The port needle 10 is a hollow needle or cannula, which is held at the hand grip element 12 and has an essentially straight section, which starts at the hand grip element 12 and ends in a tip 10A of the port needle 10. In particular, the port needle 10 is a Huber needle, which is slightly angled in the area of the cannula tip 10A, as shown in FIG. 4. In FIG. 1, the base 14 is shown in a partial region in section; the connecting structure 16 is shown fully there and not in section.

Figure 3:
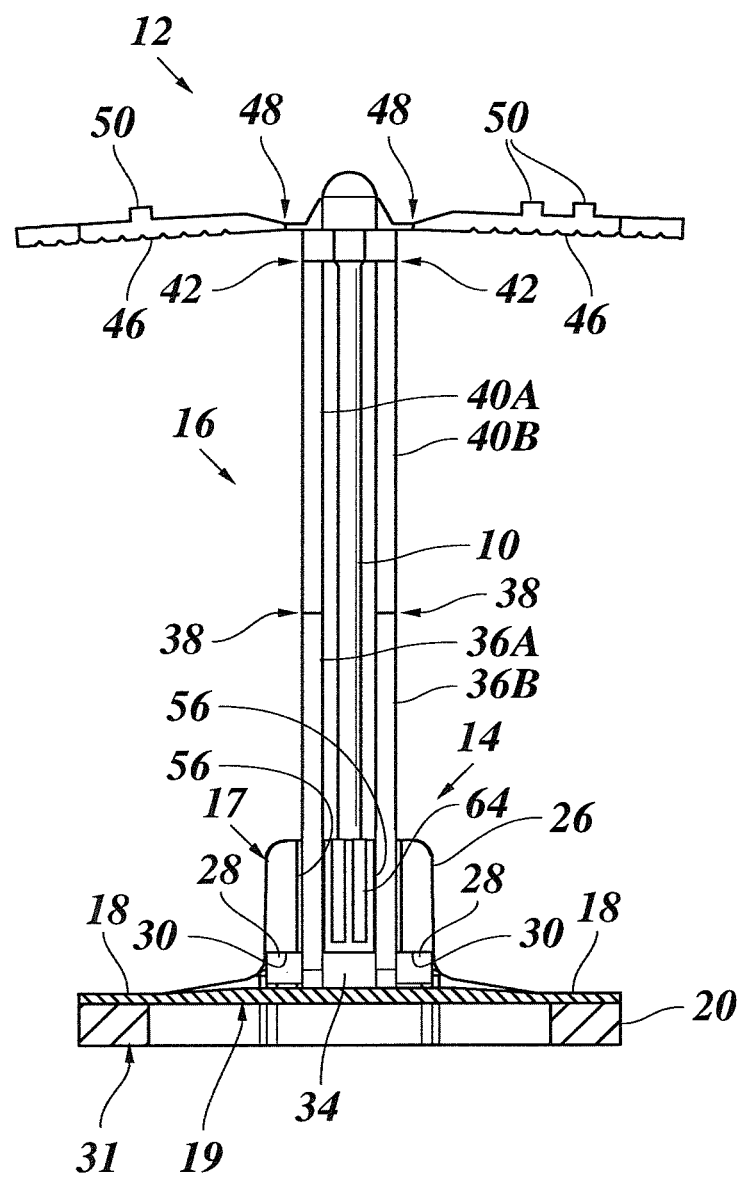
FIG. 3 shows a side view of a portion of the safety device.

As shown in FIG. 3, the base has a main body 17 and flat wings 18, which protrude laterally therefrom and are disposed at the lower edge of the base 14. The underside 19 of the base 14, which extends over the wings 18 and over the central, main body 17, is essentially flat and connected with a supporting cushion 20 of foam, for example, by gluing, which lies flat against the underside 19 of the base 14 and forms an essentially annular, broad supporting surface for supporting the base 14 on the skin of a patient. The supporting cushion 20 has a thickness, for example, of 1 to 2 mm.

At a distance from the underside 19 of the base 14, in an upper wall 22, a guide opening 24 for the cannula is recessed, into which the cannula 10 dips. The cannula 10 is guided directly, that is, without intermediate components, in the guide opening 24 with a little clearance or, preferably, without clearance.

The base essentially has the shape of a plate, from which, on the upper side, a box-shape annex 26 arises, the plate, forming the wings 18, protruding at the two opposite sides of the annex 26. The main body 17 comprises the annex 26.

With its underside end, the connecting structure 16 dips into the annex 26 of the base 14 and is mounted there with kingpins 28 on either side in kingpin receivers 30 of the base 14. The kingpins 28 form a joint axis of a swivel joint. In FIG. 1, the joint axis proceeds perpendicularly to the plane of the drawing and parallel to the supporting surface 31 of the supporting cushion 20 at the underside 19 of the base 14. In the perpendicular direction to the underside 19 of the base 14, the kingpins 28 and, with that, the joint axis are at a distance from the guide opening 24.

The internal space of the base 14, between the guide opening 24 and the height of the kingpin 28, in which, in FIG. 1, the tip 10A of the cannula 10 is disposed, is surrounded on four sides by sidewalls 32 of the annex 26, and is bounded in the upward direction by the upper wall 22. In the linearly extended position of the connecting structure, shown in FIG. 1, this internal space is closed off in the downward direction by a wall element 34, so that the tip 10A of the cannula 10 is shielded on six sides, that is, peripherally as well as at the top and at the bottom. The wall element 34 is part of the connecting structure 16 and disposed between the kingpins 28, with which it is connected firmly. In the position of FIG. 1, the wall element 34 protrudes laterally and essentially horizontally from the joint axis of the swivel joint 28, 30.

Above the kingpin 28 and at right angles to the wall element 34, two parts, 36A, 36B of a lower section 36 of the connecting structure 16 protrude parallel to one another. At their upper ends, these parts 36A, 36B are each connected over swivel joints in the form of living hinges 38 with one of two parts 40A, 40B of an upper section 40 of the connecting structure 16, which are disposed parallel to one another. At their upper ends, the parts 40A, 40B, each, in turn, are connected over a swivel joint in the form of a living hinge 42 with the hand grip element 12.

The parts 36A, 36B, 40A, 40B of the connecting structure each are elongated, stiff plastic elements and have a shielding wall 44. In each of the lower and upper sections 36, 40 of the connecting structure 16, the shielding walls 44 are opposite to one another with their flat sides. In the position shown in FIG. 1, the cannula 10 is disposed between mutually opposite shielding walls 44 and extends along the longitudinal direction of the parts 36A, 36B, 40A, 40B. By these means, the cannula 10 is shielded below the hand grip element 12 by the parts and the shielding walls 44 against access. In particular, the shaft of the needle, pulled out of the base 14 after the port needle has been used, is well shielded against access by being disposed within the tubular or channel-shaped space, which is stretched by the shielding walls 44, which are disposed on both sides.

The shielding walls 44, thus form an elongated shielding, which extends over the essential part of the length of the connecting structure 16.

Figure 2:
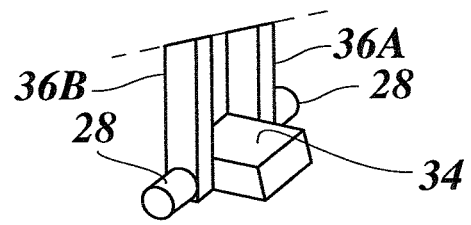
FIG. 2 shows a perspective, diagrammatic representation of a lower end of a connecting structure of the safety device.

In FIG. 1, in the viewing direction of the joint axis of the swivel joint 28, 30, the wall element 34, together with the section 36, forms an inverted L-shaped arrangement or an L-shaped arrangement. As can be seen in FIG. 2, the joint axis passes through the angle of the L shape.

FIG. 3 shows the arrangement of the cannula 10 between the linearly extended sections of the parts, 36A, 36B and 40A, 40B.

At its opposite sides, the hand grip element 12 has protruding wings 46, which are connected over living hinges 48 with a central section of the hand grip element 12 and can be folded upward against one another in a known away. In the mutually folded state, the wings 46 can be connected with one another over fixing elements 50.

The hand grip element 12, with the wings 46 as well as the connecting structure 16 with the sections of the parts 36 and 40, including the section 34 protruding transversely from the lower section and the kingpin 28, are produced in one piece from plastic as an injection molded part, preferably from a relatively flexible, soft plastic, such as polyvinyl chloride (PVC).

As shown in FIG. 1, the annex 26 of the base 14 comprises a main part 52 and an end cap 54. The main part 52 has slots for the parts 36A, 36B. The end cap 54 is connected with the main part 52, for example, over a living hinge 58.

The slots 56 as well as the kingpin receivers 30 are freely accessible when the end cap 54 is opened. FIG. 3 shows a viewing direction in FIG. 1, wherein the end cap 54 is omitted. For the installation, the end cap 54 is open and the connecting structure 16, with the port needle 10 installed, is inserted with the king pin 28 into the open kingpin receivers 30 and the slots 56. FIG. 3 shows diagrammatic fixing elements 64 of the end cap 54, which can be fixed in a fixing receiver 66 (FIG. 1) of the main part 52.

By closing and locking the end cap 54 in place, the kingpin receivers 30 are closed, so that the position of the joint axis of the kingpin 28 is fixed.

The base 14 with the wings 18 and the annex 26 is produced, for example, in one piece with the end cap 54 from a relatively hard, for example, transparent plastic, such as polyoxymethylene (POM), polycarbonate and transparent acrylonitrile butadiene styrene (ABS). In this connection, it is particularly advantageous that, due to the simple construction of the swivel joint 28, 30, with which the connecting structure 16, including the wall element 34, is mounted at the base 14, the base 14 can be produced in one piece with the end cap 54, which is connected over the living hinge.

The three joints at the ends, as well as in the center in the connecting structure 16 are swivel joints, that is, they permit joint movement precisely about one joint axis. As can be seen in FIGS. 1, 3 and 4, the joint axis of the swivel joint 28, 30, is parallel to the joint axes of the living hinges 38 and 42. The sections 36, 40, of the connecting structure 16 accordingly form a leg structure with two legs with, in each case, one knee joint in the form of a living hinge 38, a lower leg in the form of a part 36A, 36B and an upper leg in the form of a part 40A, 40B.

Figure 7:
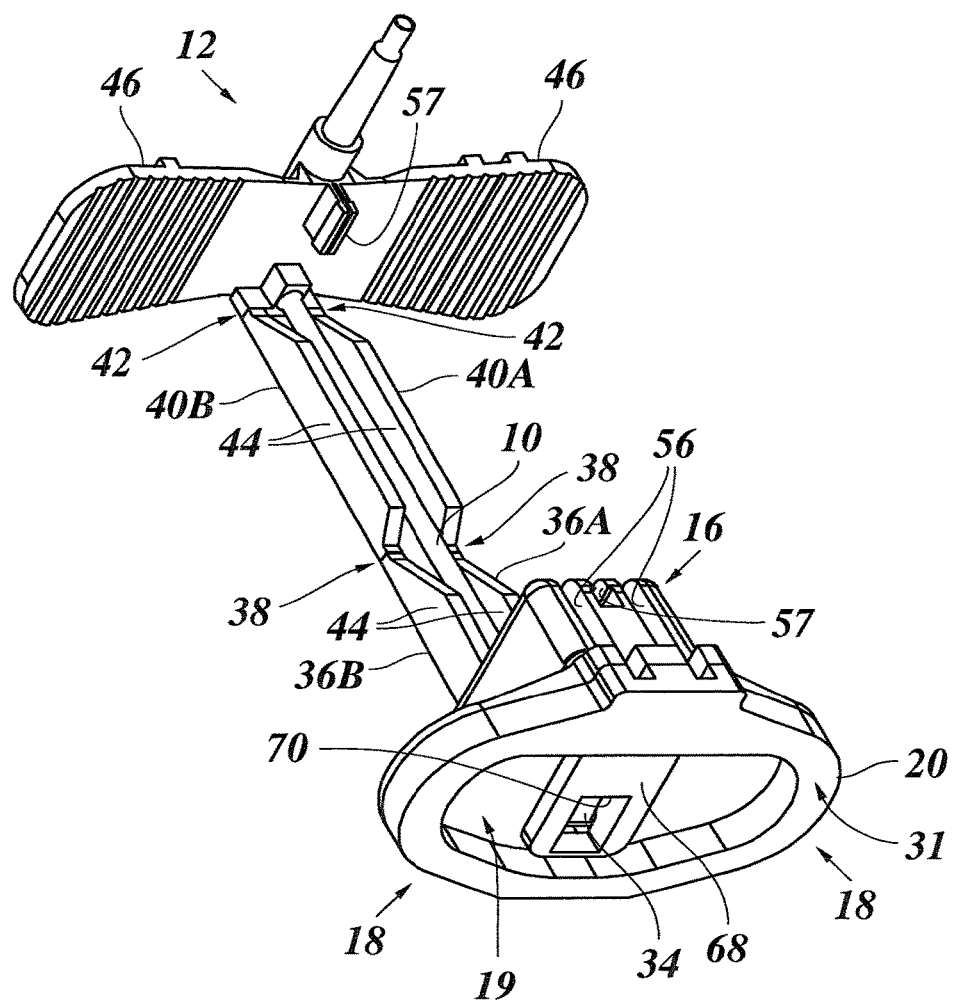
FIG. 7 shows a perspective view of the safety device in the safe state of FIGS. 1 and 3.

FIG. 4 shows a first folded together state of the connecting structure 16, for which the cannula 10 protrudes vertically with the predominant part of its length below the underside 19 of the base 14. In this ready to use position of the port needle, the parts 36A, 36B, 40A, 40B with the shielding walls 44 are taken up in the slots 56, which extend over the length of the main part 52, and protrude at the side opposite to the end cap 54 from the base 14 from the side wall 32 thereof. The hand grip element 12, with the sections 40 and 36, assumes an essentially Z-shaped, folded together position, in which the hand grip element 12 lies flat at the base 14 and is locked in place or held thereon, for example, with fixing elements 57 (FIG. 7). In the folded together position, the parts 36A, 36B cross the cannula 10, which passes through the space between the parts 36A, 36B. By these means, the wall element 34 can be swiveled from below in front of the inner space of the base, until is in the position of FIG. 1 in front of the tip 10A of the cannula. The parts, 40A, 40B also cross the cannula 10 in the position of FIG. 4.

Figure 6:
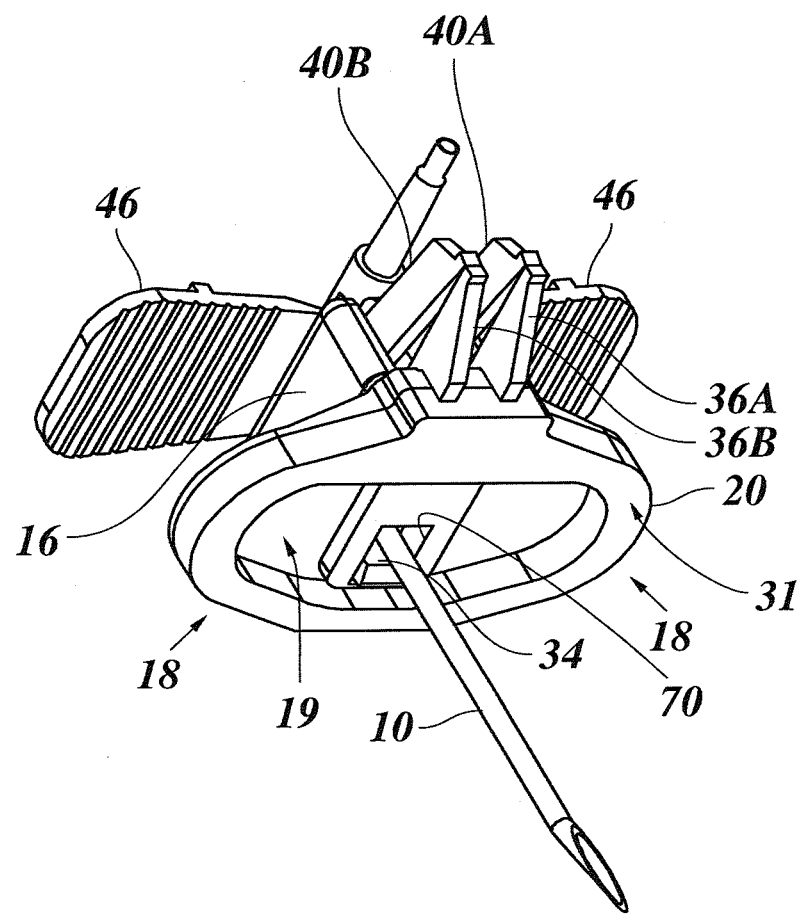
FIG. 6 shows a perspective view of the safety device in the ready to use state of FIG. 4

In the position shown in FIGS. 4 and 6, which is suitable for introducing the cannula 10 into an implanted port, the device can be fastened flat on the skin of the patient. The wall element 34 is next to the shaft of the cannula 10, as shown in FIG. 6. After the port needle is used, the wings 46, can be folded up and, by taking hold of the handle element 12 at the folded wings 46, this element is pulled up, while the base 14 is held by placing two fingers on the wings 18. During the upward motion, the cannula 10 is guided in the guide opening 24, and the connecting structure 16 is unfolded from the folded together state into the linear, extended state of FIG. 1. At the same time, the wall element 34 swivels synchronously with the swiveling motion of the parts 36A, 36B from the vertical, downwardly directed position shown in FIG. 1 into the essentially horizontal position with respect to the supporting surface 31 of the base 14. The cannula 10 slides, for example, along the wall element 34, until finally, in the end position, the tip 10A of the cannula 10 is disposed above the wall element 34 and directed, for example, in the direction of the surface of the wall element 34.

During the unfolding of the connecting structure 16 and the movement of the wall element 34 into the final position in front of the tip 10A of the cannula 10, the main body 17 of the base 14 holds the joint 28, 30 always at a fixed distance and preferably in a fixed position with respect to the upper side of the wings 18 at the lateral annex of the wings 18 at the main body 17 and therefore also at a fixed distance from the underside 19 of the base 14. There is, therefore, no upward movement of the axis of the joint 28, 30, but only a rotation. In particular, the part of the joint 28, 30, that is, the kingpin receivers 30 on the base side, is firmly connected and preferably molded in one piece with the lateral annex of the wings 18 at the main body 17 of the base 14. Accordingly, the joint 28, 30 is connected immovably with the annex of the wings 18 at the main body 17. By these means, a defined folding motion of the connecting structure 16 can take place by holding the wings 18 and pulling the cannula 10 up by means of the hand grip element 12. Accordingly, when folding the connecting structure and pulling the cannula up into the safe position of the safety device, only the connecting structure, but not the part of the base 14, surrounding the cannula, is raised partly. In particular, the guide opening 24 of the wall 22 always remains at a fixed distance and in a fixed position relative to the upper side of the wing 18 at the lateral annex of the wing 18 and therefore also at a fixed distance from the underside 19 of the base 14.

Optionally, the base 14 has a stopping projection 60, which is divided into two parts and past which the wall element is swiveled into the end position with elastic deformation of the stopping project on 60 and/or the wall element 34. In the end position, the stopping projection 60 protrudes in front of the underside of the wall element 34, so that the wall element 34 is held in position and secured in the shielding position, as shown in FIG. 1.

Figure 5:
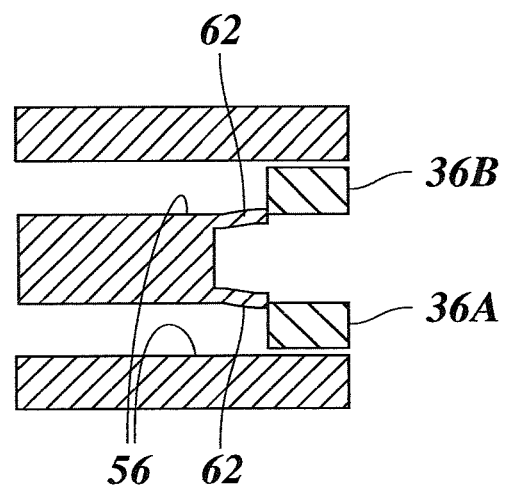
FIG. 5 shows a diagrammatic, cross-sectional view of a portion of a base of the safety device.

As shown diagrammatically in FIG. 5, the base 14 optionally has blocking elements 62, which protrude ramp-like into the slots 56. During the folding-up motion of the connecting structure 16, the parts, 36A, 36B pass over the blocking element 62 with elastic deformation of the blocking element 62 and/or an elastic evasion movement of the parts 36A, 36B. In the final position of the connecting structure 16, shown in FIGS. 1 and 5, the blocking element 62 then is disposed in front of the parts 36A, 36B, so that these are blocked to prevent swiveling back.

As the wall element 34 overcomes the stopping projection 60 and/or as the parts 36 overcome the blocking element 62, an audible clicking noise is produced, in order to indicate to the user that the safety device has reached the safe, locked, final state.

In the position of FIG. 1, particularly good protection against accidental contacting the used cannula 10 and especially the tip 10A is created by the safe arrangement of the cannula tip 10A within the base 14 and the arrangement of the shaft of the cannula 10 between the shielding walls 44. The position of the tip 10A is fixed here by the length of the connecting structure 16 in the vertical direction, whereas, in the direction transverse to the vertical direction relative to the flat underside 19 of the base 14, the position of the tip 10A of the cannula 10 is fixed by the guide opening 24 surrounding the cannula. At the same time, the cannula 10 continues to be held in the hand grip element 12.

In a perspective view obliquely from below, FIG. 6 diagrammatically shows the underside 19 of the base 14 with the annular, supporting cushion 20, which surrounds the protruding cannula 10 in the ready to use position of the port needle 10 of FIG. 4.

FIG. 7 diagrammatically shows a perspective representation of the safety device with a linearly extended connecting structure 16. The tip 10A of the cannula 10 is pulled completely into the base 14 behind the wall element 34.

As shown in FIG. 7, the base 14 has a panel-shaped surface section 68 in the area of the underside opening. This surface section 68 lies somewhat lower than the surrounding area of the underside 19 of the base 14. The surface section 68 protrudes, for example, up to half the thickness of the supporting cushion 20 downwards, so that the underside 19 of the base 14, nevertheless, is essentially flat.

FIGS. 6 and 7, furthermore, show an opening 70 in the bottom of the base 14 in the region the surface section 68, through which the cannula 10 passes when the connecting structure is folded together and in which the wall element 34 can be swiveled out of its downwardly directed position into the shielding position.

What is claimed is:

1. A safety device for shielding a medical needle, comprising:
    a hand grip element;
    a cannula, which is held at the hand grip element;
    a base with laterally protruding, flat wings, wherein the base has an underside which extends over the wings and is essentially flat and wherein the base has a guide opening which is spaced apart from the underside and in which the cannula is guided; and
    a connecting structure which connects the hand grip element with the base and comprises two elongated sections, connected in a row with one another by at least one joint, wherein the connecting structure is connected at one end by at least one joint with the hand grip element and, at an opposite end, by at least one joint with the base,
    wherein at least one said elongated section of the connecting structure is connected with the base by the at least one joint, the at least one said elongated section of the connecting structure has a wall element which protrudes transversely at a base end of the at least one said elongated section, and
    wherein the two elongated sections and the at least one joint which connects the two elongated sections is disposed so that the connecting structure is adapted to be unfolded from a first state, in which the cannula, which is guided in the guide opening of the base, protrudes with a part of its length and a tip thereof from the underside of the base with the wall element positioned in side by side adjacent relation with said cannula, into a second extended state, in which the cannula is disposed along the connecting structure, the wall element is disposed transverse to a longitudinal axis of said part of the length of the cannula in a blocking position along said longitudinal axis in front of the tip of the cannula with said longitudinal axis passing through said wall element, and a side wall of the base protectively surrounds the tip between the guide opening and the wall element and shields the tip against access,
    wherein the wall element protrudes transversely from a lower end of the at least one elongated section, is coupled directly with a lower section of at least one elongated section of the two elongated sections, and is firmly connected with a lower end of at least one elongated section of the two elongated sections to form an L-shaped arrangement with the lower end of the elongated section in the first state and in the second, at least one elongated state, and to be swiveled together with the lower end of the elongated section when unfolding the connecting structure from the first state into the second, at least one elongated state.

2. The safety device of claim 1, wherein at least one elongated section of the two elongated sections of the connecting structure comprises at least two parts which are disposed mutually opposite to one another on either side of the cannula and extend next to the cannula in a longitudinal direction of the cannula, when the connecting structure is extended linearly into the second state.

3. The safety device of claim 2, wherein the parts have shielding walls, which, with flat sides thereof, lie opposite to one another.

4. The safety device of claim 1, wherein the at least one elongated section of the two elongated sections of the connecting structure which is connected with the base by the at least one joint, comprises two parts which cross the cannula in the first state of the connecting structure, the cannula passing through a space between the parts, which are disposed next to one another and spaced apart.

5. The safety device of claim 1, wherein the at least one joint which connects the two elongated sections, and the at least one joint by which the one end of the connecting structure is connected with the hand grip element and the at least one joint by which the one end of the connecting structure is connected with the base and the base, have joint axes which are parallel to one another.

6. The safety device of claim 1, wherein a first elongated section of the two elongated sections of the connecting structure is connected at one end with the hand grip element, and, at an opposite end, with a second elongated section of the two elongated sections over at least one joint in the form of a living hinge.

7. The safety device of claim 1, wherein the at least one elongated section of the connecting structure which is connected with the base by the at least one joint, has kingpins, which are mounted in receivers of the base, the kingpins and the receivers forming the at least one joint connected to the base and the at least one elongated section.

8. The safety device of claim 7, wherein the hand grip element, the two elongated sections of the connecting structure, the wall element and the kingpins are formed together in one piece from a plastic material.

9. The safety device of 1, wherein the elongated section of the connecting structure which is connected with the base by the at least one joint, is divided in a longitudinal direction thereof into two parts, the two parts being firmly connected with one another at a base-side end of the at least one elongated section of the connecting structure over the transversely protruding wall element, and said at least one elongated section, on mutually opposite sides, has kingpins which form an axis of the joint, and the two parts, as seen in a direction of the joint axis, forming an L-shaped arrangement with the wall element.

10. The safety device of claim 9, wherein the joint axis passes through an angle of the L-shaped arrangement.

11. The safety device of claim 1, wherein the wings of the base are mounted laterally at a main body of the base, and wherein the main body of the base holds the at least one joint by which the connecting structure is connected at the opposite end with the base, at a fixed distance to an upper side of the wings at a lateral annex of the wings at the main body of the base.

12. The safety device of claim 1, wherein the connecting structure is divided along a longitudinal direction thereof and a division thereof extends over a connection of the two elongated sections, so that the connecting structure has two parts in each of the two elongated sections and wherein the two elongated sections are connected by a joint in the form of two living hinges, each of which connects one part of one elongated section of the two elongated sections with one part of the elongated section of the two elongated sections, and wherein the parts of each elongated section are disposed so that they extend mutually opposite to one another on either side of the cannula next to the cannula in a longitudinal direction of the cannula, when the connecting structure is stretched linearly in the second state.

13. The safety device of claim 1, wherein:

the at least one elongated section of the connecting structure which is connected with the base by the at least one joint, has kingpins, which are mounted in receivers of the base, the kingpins and the receivers forming the at least one joint, the hand grip element, the two elongated sections of the connecting structure, the wall element and the kingpins are formed together in one piece from a plastic material, and the elongated section of the connecting structure which is connected with the base by the at least one joint, is divided in a longitudinal direction thereof into two parts, the two parts being firmly connected with one another at a base-side end of the at least one elongated section over the transversely protruding wall element, and said at least one elongated section, on mutually opposite sides, has kingpins which form an axis of the joint, and the two parts, as seen in a direction of the at least one joint connected to the base and the connecting structures axis, forming an L-shaped arrangement with the wall element.

14. The safety device of claim 7, wherein the wall element is connected firmly with the kingpins.

* * * * *